United States Patent
Ortiz et al.

(10) Patent No.: US 10,098,728 B1
(45) Date of Patent: Oct. 16, 2018

(54) INTRAOCULAR LENS FACILITATING NON-INVASIVE POSITION ADJUSTMENT AFTER CORNEAL HEALING

(71) Applicant: NOVARTIS AG, Basel (CH)

(72) Inventors: Fernando Ortiz, Fort Worth, TX (US); Michael J. McFadden, Hurricane, WV (US)

(73) Assignee: Novartis AG, Basel (CH)

( * ) Notice: Subject to any disclaimer, the term of this patent is extended or adjusted under 35 U.S.C. 154(b) by 32 days.

(21) Appl. No.: 14/920,102

(22) Filed: Oct. 22, 2015

Related U.S. Application Data

(60) Provisional application No. 62/126,818, filed on Mar. 2, 2015.

(51) Int. Cl.
*A61F 2/16* (2006.01)

(52) U.S. Cl.
CPC ...... *A61F 2/1648* (2013.01); *A61F 2002/169* (2015.04)

(58) Field of Classification Search
None
See application file for complete search history.

(56) References Cited

U.S. PATENT DOCUMENTS

| | | | |
|---|---|---|---|
| 2003/0135271 A1* | 7/2003 | Bandhauer | A61F 2/1629 623/6.22 |
| 2009/0005865 A1* | 1/2009 | Smiley | A61F 2/1613 623/6.13 |

* cited by examiner

*Primary Examiner* — Leslie Lopez
(74) *Attorney, Agent, or Firm* — S. Brannon Latimer

(57) ABSTRACT

An intraocular lens (IOL) device includes a lens configured to be positioned along the optical axis of a patient's eye and at least one haptic configured to engage an area within the patient's eye in order to position the lens along the optical axis. The IOL device further includes an expandable haptic-lens junction coupling the at least one haptic to the lens, the expandable haptic-lens junction configured to displace the lens relative to the haptic in response to an applied energy.

14 Claims, 5 Drawing Sheets

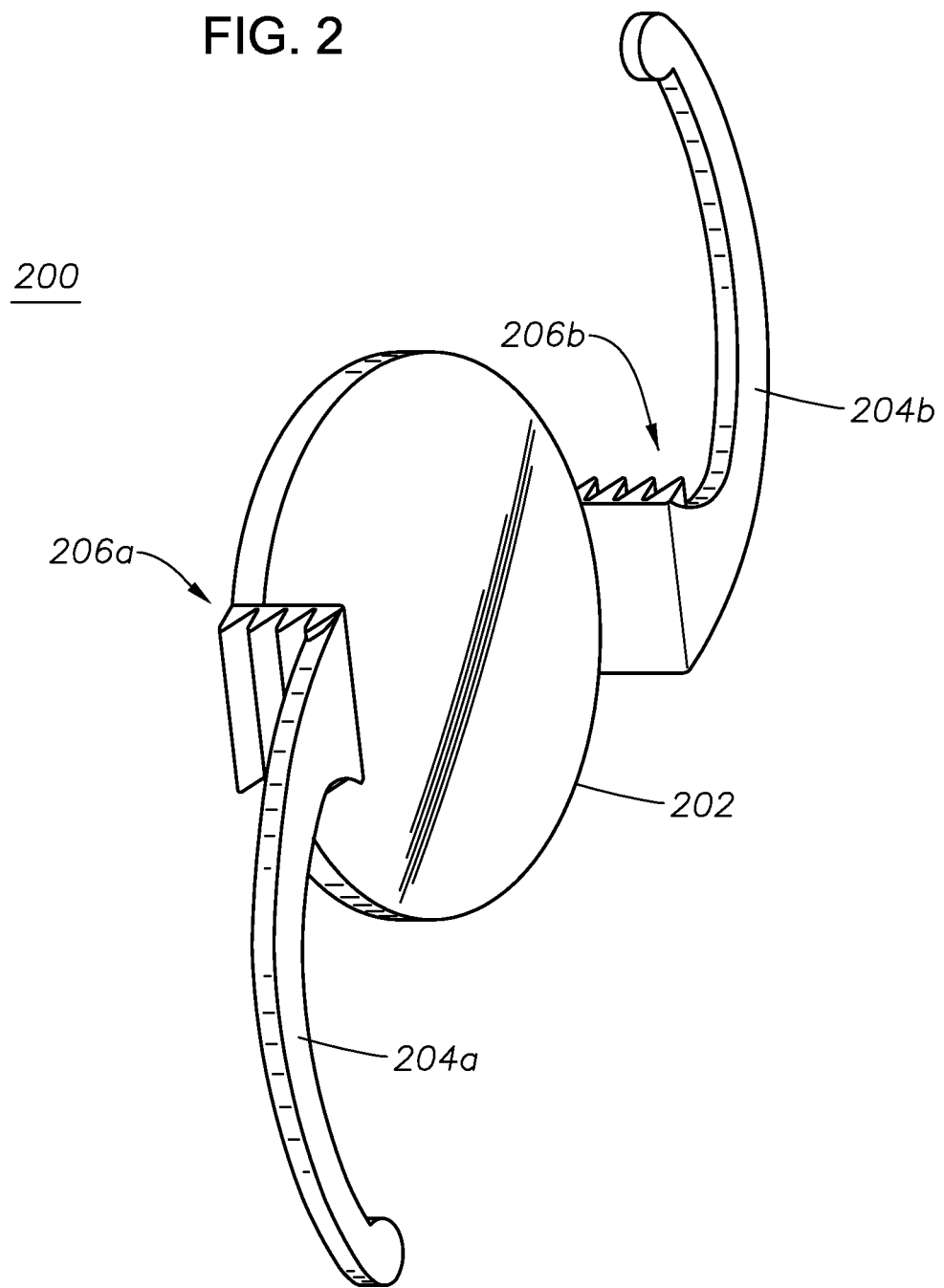

INTRAOCULAR LENS FACILITATING NON-INVASIVE POSITION ADJUSTMENT AFTER CORNEAL HEALING

FIELD

This present disclosure relates generally to cataract surgery and, more particularly, to an intraocular lens (IOL) facilitating non-invasive position adjustment after corneal healing.

BACKGROUND

Visually impairing cataract, or clouding of the lens, is the leading cause of preventable blindness in the world. Presently, cataracts are treated by surgical removal of the affected lens and replacement with an artificial intraocular lens ("IOL"). FIG. 1 is a diagram of an eye 100 illustrating anatomical structures related to the surgical removal of a cataract and the implantation of an IOL. The eye 100 comprises an opacified lens 102, an optically clear cornea 104, and an iris 106. A lens capsule (capsular bag 108) located behind the iris 106 of the eye 100 contains the opacified lens 102. More particularly, the opacified lens 102 is seated between an anterior capsule segment (anterior capsule 110) and a posterior capsular segment (posterior capsule 112). The anterior capsule 110 and the posterior capsule 112 meet at an equatorial region 114 of the capsular bag 108. The eye 100 also comprises an anterior chamber 116 located in front of the iris 106 and a posterior chamber 118 located between the iris 106 and the capsular bag 108.

A common technique for cataract surgery is extracapsular cataract extraction ("ECCE"), which involves the creation of an incision near the outer edge of the cornea 104 and an opening in the anterior capsule 110 (i.e., an anterior capsulotomy) through which the opacified lens 102 is removed. The lens 102 can be removed by various known methods. One such method is phacoemulsification, in which ultrasonic energy is applied to the lens to break it into small pieces that are aspirated from the capsular bag 108. Thus, with the exception of the portion of the anterior capsule 110 that is removed in order to gain access to the lens 102, the capsular bag 108 may remain substantially intact throughout an ECCE. The intact posterior capsule 112 provides a support for the IOL and acts as a barrier to the vitreous humor within the posterior chamber 120 of the eye 100.

Following removal of the opacified lens 102, an artificial IOL, which may be designed to mimic the transparency and refractive function of a healthy lens, is typically implanted within the capsular bag 108 through the opening in the anterior capsule 110. The IOL may be acted on and held in a desired position by the zonular forces exerted by a ciliary body 122 and attached zonules 124 surrounding the periphery of the capsular bag 108.

The power of the artificial IOL chosen for a particular patient may be selected by a surgeon based on the measured optical characteristics of the patient's eye and the desired location of the IOL along the patient's optical axis following implantation. Despite the surgeon's best efforts, however, corneal healing after cataract surgery may change the refractive properties of the eye. Additionally, the healing process may result in IOL displacement within the capsular bag 108. Corneal healing and lens displacement may cause refractive errors after cataract surgery, prohibiting a desired refraction target from being achieved. Conventional techniques for correcting post cataract surgery refractive errors (e.g., LASIK-type procedures) may be insufficient as such procedures are similarly impacted by post-surgical corneal shape change.

SUMMARY

In general, the present disclosure relates to an IOL that facilitates optical power modification after the healing process is complete without the need for further surgical intervention. In particular, an IOL according to the present disclosure includes a lens portion that may be displaced along the optical axis while implanted in the eye using non-invasive techniques (e.g., via laser energy applied to a portion of the IOL).

In certain embodiments, an IOL device includes a lens configured to be positioned along the optical axis of a patient's eye and at least one haptic configured to engage an area within the patient's eye in order to position the lens along the optical axis. The IOL device further includes an expandable haptic-lens junction coupling the at least one haptic to the lens, the expandable haptic-lens junction configured to displace the lens relative to the haptic in response to an applied energy.

Certain embodiments of the present disclosure may provide one or more technical advantages. For example, embodiments of the present disclosure may allow a surgeon to non-invasively adjust the positioning of the IOL within the patient's eye after the healing process is complete. As a result, the surgeon may compensate for refractive errors induced by the corneal healing process (which may affect the positioning of the IOL and/or the refractive properties of the cornea), allowing a higher percentage of patient's to achieve a target refraction. Additionally, the adjustability of IOLs of the present disclosure may facilitate compensation for changes in the shape of the eye resulting from the aging process.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein:

FIG. 2 illustrates an exemplary IOL device facilitating non-invasive position adjustment, according to certain embodiments of the present disclosure;

Figure 1:
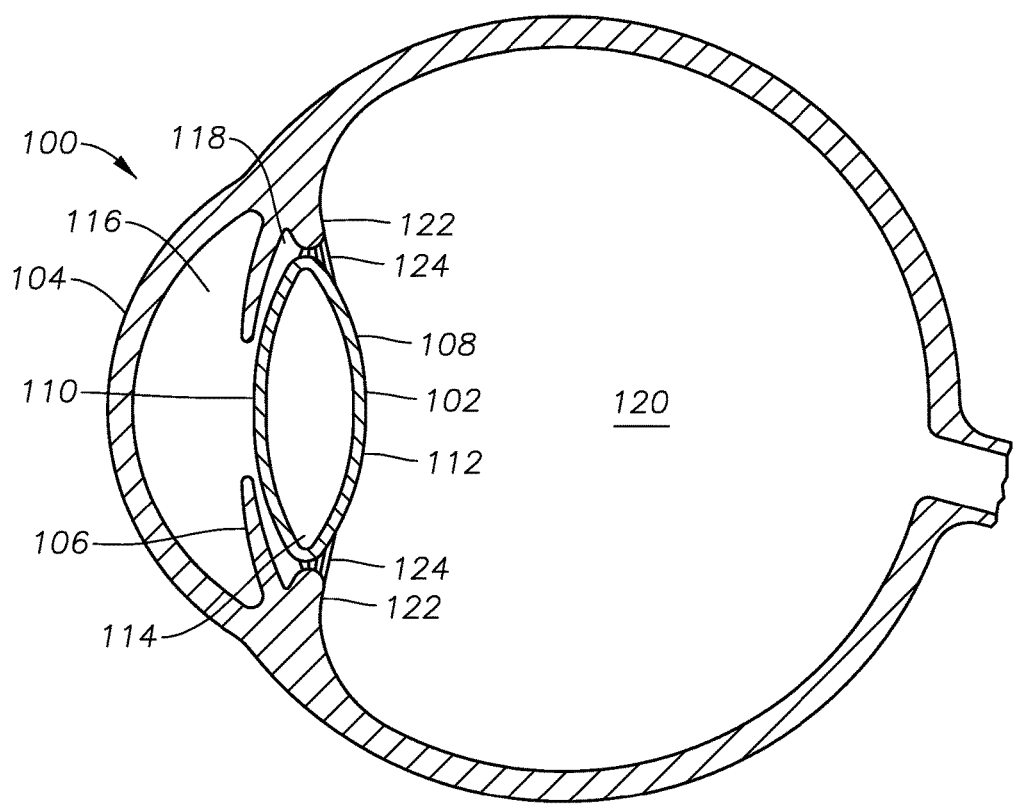
FIG. 1 is a diagram of an eye illustrating anatomical structures related to the surgical removal of a cataract and the implantation of an IOL.

The skilled person in the art will understand that the drawings, described below, are for illustration purposes only. The drawings are not intended to limit the scope of the applicant's disclosure in any way.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

In general, the present disclosure relates to an IOL that facilitates optical power modification after the healing process is complete without the need for further surgical intervention. In particular, an IOL according to the present disclosure includes a lens portion that may be displaced along the optical axis while implanted in the eye using non-invasive techniques (e.g., via laser energy applied to a portion of the IOL).

FIG. 2 illustrates an exemplary IOL device 200 facilitating non-invasive position adjustment, according to certain embodiments of the present disclosure. IOL device 200 generally includes a lens 202 configured to be positioned along the optical axis of a patient's eye and at least one haptic 204 configured to engage an area within the patient's eye in order to position the lens 202. The at least one haptic 204 is coupled to the lens 202 via an expandable haptic-lens junction 206. The expandable haptic-lens junction 206 is configured to displace the lens 202 relative to the haptic 204 in response to an applied energy (such as energy provided by an ophthalmic laser, as discussed in further detail below). As a result, IOL 200 may provide a surgeon with the ability to fine tune the placement of the lens 202 along the optical axis after the healing process is complete and without the need for surgical intervention, thereby increasing the percentage of patients achieving a target refraction.

The present disclosure contemplates that IOL device 200 may be any suitable device adapted to be inserted into a patient's eye to correct vision. IOL device 200 may be a phakic IOL designed to be used in conjunction with the natural lens of a patient's eye to correct refractive errors such as myopia (near-sightedness), hyperopia (far-sightedness) astigmatism, coma or other higher order refractive errors (blurred vision due to poor light focusing on the retina due to an irregularly shaped cornea or, in some instances, an irregularly shaped natural lens). In such embodiments, IOL device 200 may be inserted into either the anterior chamber 116 or posterior chamber 118, and may be supported by one or more of the sulcus and the iris 106. Alternatively, IOL device 200 may be an aphakic or pseudophakic IOL that is inserted in the eye subsequent to removal of the natural lens due to disease (e.g., a cataract or clouding of the natural lens) and may restore, improve, or partially correct vision by providing a power comparable to that of the natural lens (as well as correcting myopia, hyperopia or other refractive errors). In such embodiments, IOL device 200 may be inserted into the capsular bag 108 of the patient's eye after removal of the natural lens. Although the present disclosure contemplates that IOL device 200 may be either phakic or aphakic, for purposed of simplicity it is assumed throughout the remainder this description that IOL device 200 is an aphakic configured for implantation into the capsular bag 108 of a patient's eye.

Lens 202 of IOL device 200 may comprise any suitable lens for replacing a natural lens removed from a patient's eye and/or correcting errors in a patient's vision. For example, one or both surfaces of lens 202 may be curved such that the lens has an optical power corresponding to the patient's eye (such that light is properly focused on the retina). Additionally, lens 202 may have other features (e.g., spherical, aspheric, or toric features, as is known in the art) to further correct defects in the patient's vision.

Lens 202 may be coupled to one or more haptics 204, which may comprise any suitable structures designed, when implanted into a patient's eye, to engage a portion of the eye (e.g., a portion of the capsular bag 108) in order to position the lens 202 along the optical axis. For example, as depicted in FIG. 2, IOL device 200 may include two curved haptics 204a and 204d designed to engage an equatorial region of the capsular bag 108 when IOL device 200 is implanted therein. As a result, haptics 204a and 204b may substantially center lens 202 on the visual axis of the patient's eye. Although the present disclosure contemplates that IOL device 200 may include any suitable number of haptics 204 having any suitable shape for positioning lens 202, for simplicity it will be assumed throughout the remainder of this description that IOL device 200 includes two haptics (204a and 204b), as depicted in FIG. 2.

Figure 3A:
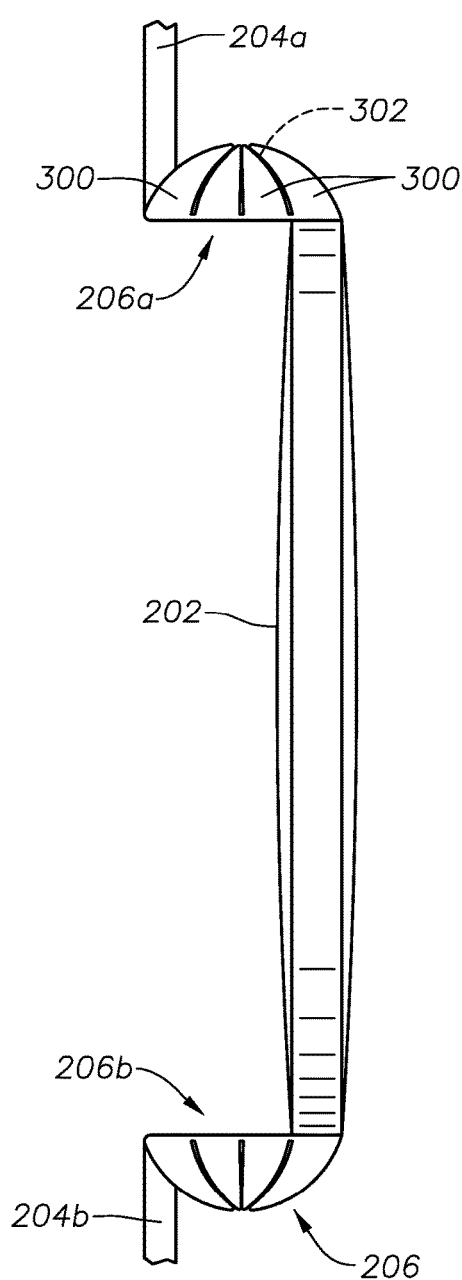
FIGS. 3A-3B illustrate detailed views of an exemplary expandable haptic-lens junction of the IOL device depicted in FIG. 2, according to certain embodiments of the present disclosure.
Figure 3B:
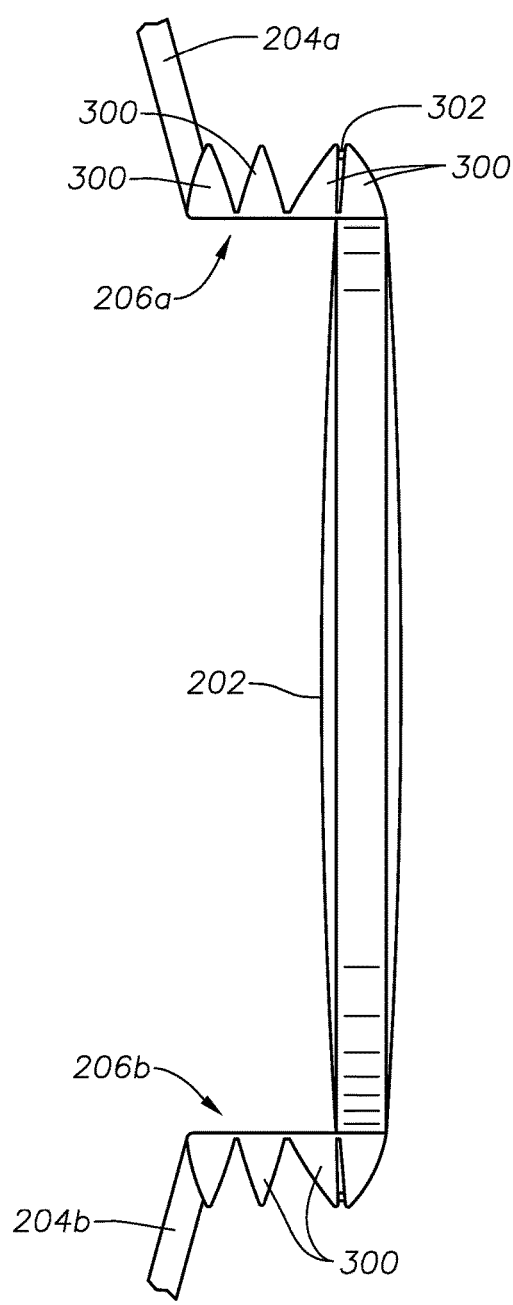

Haptics 204 may each be coupled to lens 202 via an expandable haptic-lens junction 206. Each haptic-lens junctions 206 may comprise any suitable structure for displacing lens 202 relative to the corresponding haptic 204 in response to an applied energy. FIGS. 3A-3B illustrate detailed views of an exemplary expandable haptic-lens junction 206 of the IOL device 200, according to certain embodiments of the present disclosure. More particularly, FIG. 3A illustrates an exemplary expandable haptic-lens junction 206 in a fully compressed state (e.g., as implanted at the time of cataract surgery) while FIG. 3B illustrates the exemplary expandable haptic-lens junction 206 is a partially decompressed state (e.g., after non-invasive post-cataract surgery adjustment).

Each haptic-lens junction 206 of IOL device 200 may comprise a plurality of bellows 300. As illustrated in FIG. 3A, in the fully compressed state, each of the plurality of bellows 300 may be coupled to one or more adjacent bellows 300 by a connection 302. As a result, absent the application of an external force (e.g., laser energy supplied by an ophthalmic laser), connections 302 may maintain each haptic-lens junction 206 in the compressed state.

Each haptic-lens junction 206 may be expanded by breaking one or more of the connections 302 between adjacent bellows 300 by applying an energy to those connections 302. For example, an ophthalmic laser may be used to sever one or more connections 302, thereby allowing the bellows to expand (as illustrated in FIG. 3B). As one particular example, a Neodymium Yttrium-Aluminum-Garnet ("Nd/YAG") laser may be used to sever the one or more connections 302. As another particular example, a femtosecond laser may be used to sever the one or more connections 302.

Figure 4A:
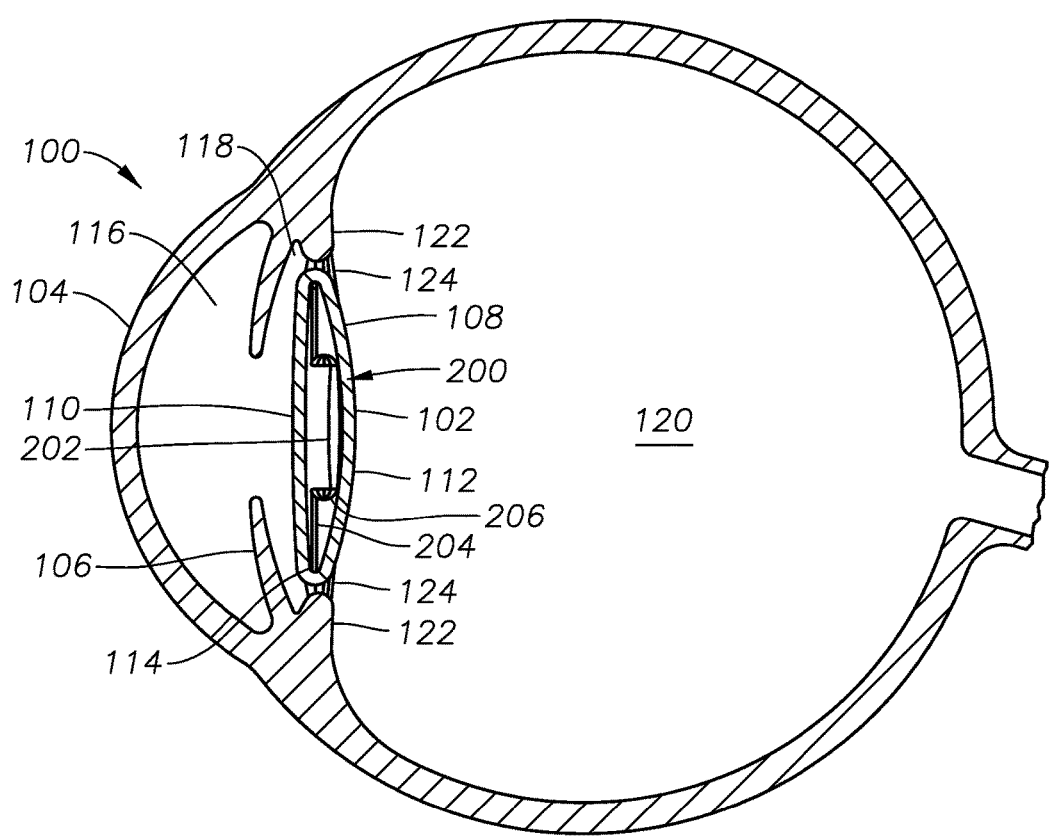
FIGS. 4A-4B illustrate the IOL device depicted in FIG. 2 after implantation into the capsular bag of a patient's eye, according to certain embodiments of the present disclosure.
Figure 4B:
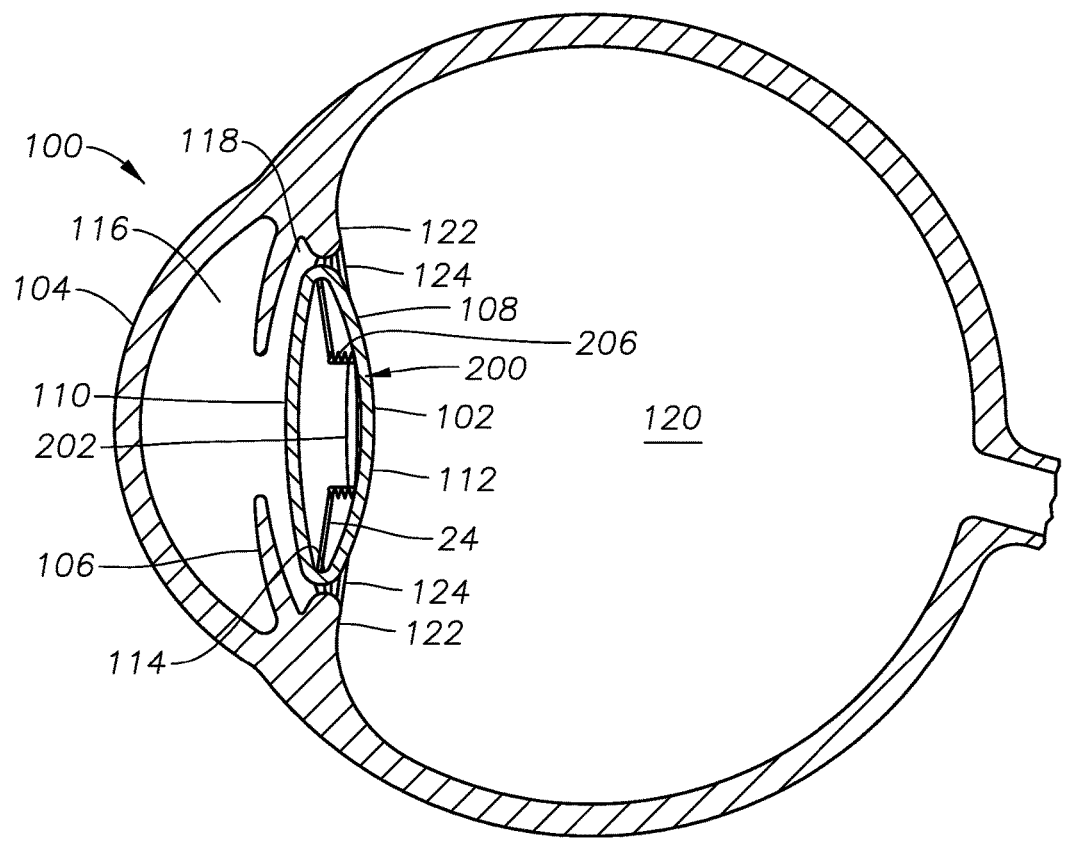

By fully or partially expanding the haptic-lens junctions 206, the lens 202 may be moved relative to the haptics 204. In embodiments having two haptics 204a and 204b, breaking equal number of connections in both haptic-lens junctions 206a and 206b may allow a surgeon to post-surgically move the lens 202 along the optical axis to achieve a target refraction that may have been missed due to post-surgical movement of the IOL device 200 due to the healing process and/or changes in the optical properties due to the healing process. In certain embodiments (as illustrated in FIGS. 4A-4B below), IOL device 200 may be implanted in the capsular bag 108 such that expanding haptic-lens junctions 206a and 206b may cause posterior movement of the lens 200 along the optical axis. Accordingly, myopic errors induced by the healing process may be corrected. Additionally, by breaking unequal numbers of connections in haptic-lens junctions 206a and 206b, a surgeon may adjust the angle of the lens 202 relative to the optical axis.

Although haptic-lens junctions 206 having a particular structure are depicted and described, the present disclosure contemplates that haptic-lens junctions 206 may have any suitable expandable structure facilitating movement of lens 202 relative to haptics 204.

IOL device 200 and components thereof may be constructed from one or more biocompatible materials. In particular, lens 202 may be constructed of a material that is optically transparent and smooth (e.g., an optical-quality surface). Exemplary materials include hydrogels, silicones, acrylic materials, and other elastomeric polymers and soft plastics. For example, the silicone materials can be unsaturated terminated siloxanes, such as vinyl terminated siloxanes or multi-vinyl terminated siloxanes. Non-limiting examples include vinyl terminated diphenylsiloxane-dimethylsiloxane copolymers, vinyl terminated polyphenylmethylsiloxanes, vinyl terminated phenylmethylsiloxane-diphenyidimethylsiloxane copolymers, vinyl terminated polydimethylsiloxanes and methacrylate, and acrylate functional siloxanes. In other embodiments the lens-forming materials can be a hydrogel or a hydrophobic acrylic, such as the AcrySof® acrylic. Use of elastic/flexible materials can also enable the IOL device 200 to be folded upon itself during implantation, thereby decreasing the size of the incision required to insert the IOL device 200 into the capsular bag 108.

FIGS. 4A-4B illustrate IOL device 200 after implantation into the capsular bag 108 of a patient's eye 100, according to certain embodiments of the present disclosure. More particularly. FIG. 4A illustrates IOL device 200 immediately after implantation (i.e., with haptic-lens junctions 206 in a fully compressed state), and FIG. 4B illustrates IOL device 200 after the healing process is complete and non-surgical adjustment of the IOL device 200 has been made (i.e., with haptic-lens junctions 206 in a partially decompressed state). As shown in FIG. 4B, lens 202 may be moved posteriorly along the optical axis by breaking one or more connections 302 in each of the haptic-lens junctions 206. Accordingly, a surgeon may adjust IOL device 200 to correct myopic errors without the need for further surgical intervention.

Although IOL device 200 has been depicted and described as being implanted in the capsular bag 108 with a particular orientation, the present disclosure contemplates IOL device 200 being implanted in the capsular bag 108 with any suitable orientation, according to particular needs.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An intraocular lens (IOL) device, comprising:
a lens configured to be positioned along an optical axis of a patient's eye, the lens comprising an anterior surface having an anterior surface curvature and a posterior surface having a posterior surface curvature;
at least one haptic configured to engage an area within the patient's eye in order to position the lens along the optical axis of the patient's eye;
an expandable haptic-lens junction coupling the at least one haptic to the lens, the expandable haptic-lens junction configured to displace the lens relative to the haptic in response to an applied energy, wherein the displacement of the lens relative to the haptic adjusts a position of the lens along the optical axis in a manner that does not change the anterior surface curvature or the posterior surface curvature, wherein the expandable haptic-lens junction comprises a plurality of bellows held in a compressed state via a plurality of connections each connecting adjacent ones of the bellows.

2. The IOL device of claim 1, wherein the applied energy breaks one or more of the plurality of connections, thereby causing at least partial decompression of the plurality of bellows.

3. The IOL device of claim 2, wherein the at least partial decompression of the plurality of bellows causes the displacement of the lens relative to the haptic.

4. The IOL device of claim 1, wherein the applied energy comprises laser energy.

5. The IOL device of claim 4, wherein the laser energy is generated by a Neodymium Yttrium-Aluminum-Garnet ("Nd/YAG") laser.

6. The IOL device of claim 1, wherein the at least one haptic is configured to engage a portion on a capsular bag of the patient's eye.

7. An intraocular lens (IOL) device, comprising:
a lens configured to be positioned along an optical axis of a patient's eye, the lens comprising an anterior surface having an anterior surface curvature and a posterior surface having a posterior surface curvature;
a first haptic configured to engage a first area within the patient's eye;
a second haptic configured to engage a second area within the patient's eye;
a first expandable haptic-lens junction coupling the first haptic to the lens, the first expandable haptic-lens junction configured to displace the lens relative to the first haptic in response to a first amount of energy applied to the first expandable haptic-lens junction; and
a second expandable haptic-lens junction coupling the second haptic to the lens, the second expandable haptic-lens junction configured to displace the lens relative to the second haptic in response to a second amount of energy applied to the second expandable haptic-lens junction;
wherein the displacement of the lens relative to the first haptic and the displacement of the lens relative to the second haptic collectively adjusts a position of the lens along the optical axis in a manner that does not change the anterior surface curvature or the posterior surface curvature;
wherein the first and the second expandable haptic-lens junctions each comprise a plurality of bellows held in a compressed state via a plurality of connections each connecting adjacent ones of the bellows.

8. The IOL device of claim 7, wherein, with regard to either the first or the second expandable haptic-lens junction, the first or the second amount of energy breaks one or more of the plurality of connections, thereby causing at least partial decompression of the plurality of bellows.

9. The IOL device of claim 8, wherein, with regard to either the first or the second expandable haptic-lens junction, the at least partial decompression of the plurality of bellows causes the displacement of the lens relative to either the first haptic or the second haptic.

10. The IOL device of claim 7, wherein each of the first and the second amounts of energy comprises an amount of laser energy.

11. The IOL device of claim 10, wherein the laser energy is generated by a Neodymium Yttrium-Aluminum-Garnet ("Nd/YAG") laser.

12. The IOL device of claim 7, wherein the first and the second haptics are each configured to engage a portion on a capsular bag of the patient's eye.

13. The IOL device of claim 7, wherein:
breaking, via the first and the second amounts of energy, equal numbers of the plurality of connections in both the first and the second expandable haptic-lens junctions adjusts the position of the lens along the optical axis without changing an orientation angle of the lens relative to the optical axis.

14. The IOL device of claim 7, wherein:
breaking, via the first amount of energy a first number of the plurality of connections in the first expandable haptic-lens junction and breaking, via the second amount of energy a second number of the plurality of connections in the second expandable haptic-lens junction, wherein the first and the second numbers are different from one another; wherein the breakings facilitate adjustment of an orientation angle of the lens relative to the optical axis.

* * * * *